(12) United States Patent
Jiang et al.

(10) Patent No.: US 7,519,419 B2
(45) Date of Patent: Apr. 14, 2009

(54) MATERIAL AND METHOD OF FORMING YTTRIA-STABILIZED ZIRCONIA TO MINIMIZE LOW-TEMPERATURE DEGRADATION

(75) Inventors: Guangqiang Jiang, Castaic, CA (US);
Kate E. Purnell, Valencia, CA (US);
Gary D. Schnittgrund, Granada Hills, CA (US)

(73) Assignee: Alfred E. Mann Foundation for Scientific Research, Santa Clara, CA (US)

( * ) Notice: Subject to any disclaimer, the term of this patent is extended or adjusted under 35 U.S.C. 154(b) by 1000 days.

(21) Appl. No.: 10/629,291

(22) Filed: Jul. 28, 2003

(65) Prior Publication Data

US 2004/0181270 A1 Sep. 16, 2004

Related U.S. Application Data

(60) Provisional application No. 60/453,682, filed on Mar. 10, 2003.

(51) Int. Cl.
*A61N 1/375* (2006.01)
(52) U.S. Cl. .......................................... 607/2; 501/105
(58) Field of Classification Search ................... 607/36; 428/697, 701, 702; 501/103, 105, 107
See application file for complete search history.

(56) References Cited

U.S. PATENT DOCUMENTS

| | | | |
|---|---|---|---|
| 4,587,225 A * | 5/1986 | Tsukuma et al. ............. | 501/105 |
| 5,193,540 A | 3/1993 | Schulman et al. | |
| 5,324,316 A | 6/1994 | Schulman et al. | |
| 5,677,072 A * | 10/1997 | Chatterjee et al. ........... | 428/701 |

(Continued)

FOREIGN PATENT DOCUMENTS

JP 2001 302345 A 4/2002

(Continued)

OTHER PUBLICATIONS

Thompson, I. and Rawlings, R.D.; "Mechanical Behavious of Zirconia and Zirconia-Toughened Aluminia in a Simulated Body Environment"; Biomaterials; 1990; 505-508; vol. II, Issue 7.

(Continued)

*Primary Examiner*—Carl H Layno
*Assistant Examiner*—Brian T Gedeon
(74) *Attorney, Agent, or Firm*—Gary D. Schnittgrund

(57) ABSTRACT

The invention is directed to a material and a method of substantially eliminating destructive low-temperature, humidity-enhanced phase transformation of yttria-stabilized zirconia in general, as well as eliminating low-temperature degradation of yttria-stabilized tetragonal zirconia polycrystalline ceramic (Y-TZP). The martensitic-type phase transformation from tetragonal to monoclinic is accompanied by severe strength degradation in a moist environment at low-temperature, specifically at room temperature as well as at body temperature. This class of materials has been chosen as the packaging material for small implantable neural-muscular sensors and stimulators because of the high fracture toughness and high mechanical strength. This destructive phase transformation has been substantially eliminated, thus ensuring the safety of long-term implants, by subjecting the sintered components to post-machining hot isostatic pressing, such that the average grain size is less than about 0.5 microns.

27 Claims, 2 Drawing Sheets

U.S. PATENT DOCUMENTS

| | | | | |
|---|---|---|---|---|
| 5,688,731 | A | * | 11/1997 | Chatterjee et al. .......... 501/96.3 |
| 6,011,993 | A | * | 1/2000 | Tziviskos et al. ............. 607/36 |
| 6,069,103 | A | | 5/2000 | Kwon |
| 6,735,475 | B1 | * | 5/2004 | Whitehurst et al. ........... 607/46 |
| 2002/0013625 | A1 | | 1/2002 | Cales et al. |

FOREIGN PATENT DOCUMENTS

| | | |
|---|---|---|
| JP | 2002 362972 A | 4/2003 |
| WO | WO 01/80783 A | 11/2001 |

OTHER PUBLICATIONS

Drummond, J.; "In Vitro Aging of Yttria-Stablized Zirconia"; J. Am. Ceram. Soc.; 1989; 675-676; 72 [4].

Drummond, J.; "Effects of In Vitro Aging of Magnesia-Stablized Zirconia"; J. Am. Ceram. Soc.; 1992; 1278-1280; 75 [5].

Piconi, C. and Maccauro, G.; "Zirconia as a Ceramic Biomaterial"; Biomaterials; 1999; 1-25; 20.

Jiang, Accelerated Life Testing of Y-TZP Ceramic, Proceedings of the 6th Annual Grodins Graduate Research Symposium, Biomedical Engineering Department, USC, Los Angeles, California, Mar. 23, 2002, pp. 70-71.

Jiang, In-Vitro and In-Vivo Aging Tests of BION Micro-Stimulator, Proceedings of the 7th Annual Grodins Graduate Research Symposium, Biomedical Engineering Department, USC, Los Angeles, California, Mar. 29, 2003, pp. 3-4.

Jiang, In-Vitro and In-Vivo Test of 3Y-TZP Ceramics, Oral Presentation at the 54th Pacific Coast Regional Basic Science Division Meeting of the American Ceramic Society, Seattle, Washington, Oct. 1-4, 2002, pp. 1-5.

* cited by examiner

MATERIAL AND METHOD OF FORMING YTTRIA-STABILIZED ZIRCONIA TO MINIMIZE LOW-TEMPERATURE DEGRADATION

CROSS REFERENCE TO RELATED APPLICATION

This application claims the benefit of U.S. Provisional Application Ser. No. 60/453,682, filed on Mar. 10, 2003.

FIELD OF THE INVENTION

This invention relates to a material and a method of increasing the useful life of an yttria-stabilized zirconia structure when implanted in living tissue.

BACKGROUND OF THE INVENTION

A widely employed bioceramic is alumina, which is classed as bioinert. The search for an ideal bioceramic has included alumina, hydroxyapatite, calcium phosphate, and other ceramics. The first use of aluminas for implants in orthopedics and dentistry was in the 1960's and they were employed in hip prostheses as early as 1970. Since those early days the quality and performance of aluminas have improved and high-purity, high-density, fine-grained aluminas are currently used for a wide range of medical applications, e.g. dental implants, middle ear implants, and hip or knee prostheses.

Although the aluminas currently available perform satisfactorily, a further improvement in strength and toughness would increase the safety factor and may extend usage to higher stressed components. A proposed candidate to add to this list is stabilized-zirconia because of its potential advantage over alumina of a lower Young's modulus, higher strength, and higher fracture toughness. Another advantage of stabilized-zirconia is low-wear residue and low coefficient of friction. Zirconia undergoes a destructive phase change at 1000° to 1100° C. from monoclinic to tetragonal, which necessitates phase stabilization by calcia, magnesia, ceria, or yttria.

Tetragonal zirconia polycrystalline ceramic, commonly known as TZP, which typically contains 3 mole percent yttria, coupled with the small size of the particles, results in the metastable tetragonal state at room temperature. Under the action of a stress field in the vicinity of a crack, the metastable particles transform, with a 3% to 4% volume increase, by a shear-type reaction, to the monoclinic phase. Crack propagation is retarded by the transforming particles at the crack tip and by the compressive back stress on the crack walls behind the tip, due to volume expansion associated with transformation to the monoclinic phase.

The well-known transformation toughening mechanism is operative in zirconia ceramics whose composition and production are optimized such that most of the grains have the tetragonal crystal structure. These zirconias are referred to as tetragonal zirconia polycrystal (TZP) ceramics and their mechanical properties in air at room temperature are superior to those of zirconia-toughened aluminas and to other classes of zirconias. To the knowledge of the inventors, the biocompatibility of TZPs has not been fully assessed. However, the biocompatibility of the TZP has been at least preliminarily investigated.

For example, in one study by Thompson and Rawings [see I. Thompson and R. D. Rawlings, "Mechanical Behavior of Zirconia and Zirconia-Toughened Alumina in a Simulated Body Environment," Biomaterials, 11 [7] 505-08 (1990)]. The results that TZP demonstrated a significant strength decrement when aged for long periods in Ringer's solution and was therefore unsuitable as implant material.

Drummond [see J. L. Drummond, J. Amer. Ceram. Soc., 72 [4] 675-76 (1989)] reported that yttria-stabilized zirconia demonstrated low-temperature degradation at 37° C. with a significant decrement in strength in as short as period as 140 to 302 days in deionized water, saline, or Ringer's solution. He also reports on similar observation by others, where yttria-doped zirconia demonstrated a strength decrement in water vapor, room temperature water, Ringer's solution, hot water, boiling water, and post-in vivo aging.

TZP components suffer a decrement in strength properties after exposure for only a few days to humid environments. This degradation of mechanical properties occurs when moisture is present in any form, for example, as humidity or as a soaking solution for the TZP component. TZP components have been observed to spontaneously fall apart after times as short as a few weeks in room temperature water. This is of particular importance in living-tissue implanted devices that contain components made of this class of material. Successful long-term implantation of devices that contain yttria-stabilized zirconia components is not feasible.

DETAILED DESCRIPTION OF THE PREFERRED EMBODIMENT

A broadly applicable material and method of producing the improved material has been developed. It has been demonstrated that hot isostatic pressing a sintered yttria-stabilized tetragonal zirconia polycrystalline ceramic (Y-TZP) dramatically reduces the destructive phase transformation from tetragonal to monoclinic. While this material and the method of production are widely applicable, a preferred embodiment is to apply this invention to implantable devices that are suitable for use as implants in living tissue, an application previously prohibited to this class of ceramic material.

A novel ceramic to metal brazed case has been designed for implantable microstimulator, such as the microstimulator of Advanced Bionics Corporation, 12740 San Fernando Road, Sylmar, Calif. U.S. Pat. No. 5,193,540 and 5,324,316 present developments related to this microstimulator and are incorporated in their entirety by reference herein. Yttria stabilized-TZP (Y-TZP) has been selected as the ceramic material because of its high strength, favorable fracture toughness, and biocompatibility. It provides a hermetic and robust housing for the electronic module located inside.

The strength decrement in humid environment varies among Y-TZP ceramics, depending upon the quality of the ceramic and its composition. This variability is related to the differences in equilibrium of microstructural parameters such as: concentration and distribution of phase stabilizer, grain size, flaw population and distribution, residual stress, density, etc.

Figure 1:
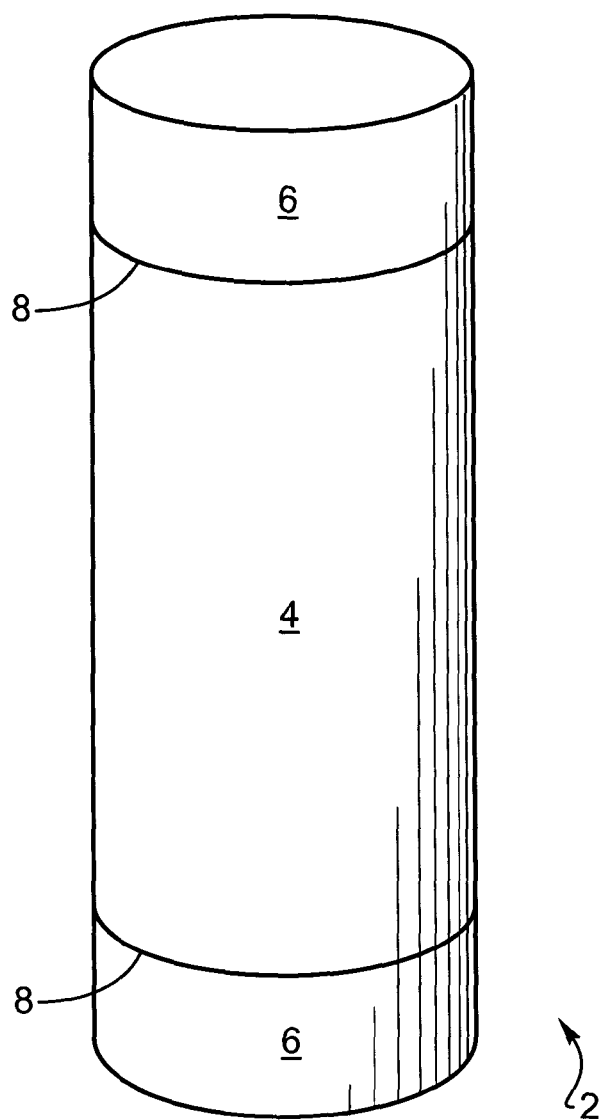
FIG. 1 presents the microstimulator.

A preferred microstimulator 2 is presented in FIG. 1, wherein a hollow ceramic tube 4 is preferably attached by brazing to an electrode 6 on either end of the microstimulator 2, thereby forming a hermetically sealed hollow enclosure suitable to contain electronics for either sensing or stimulating living tissue into which the microstimulator 2 may be implanted. The size of the microstimulator 2 is preferably approximately 10 mm or less in diameter and 100 mm or less in length, preferably less than 6 mm in diameter and 60 mm in length, and of longitudinal shape capable of implantation in the immediate vicinity of selected areas of the body by expulsion through a hypodermic needle or other implantation device.

The ceramic tube 4 is comprised of a strong, hermetic material that is biocompatible, such as Y-TZP. In alternative embodiments, other stabilizer materials may be utilized in place of yttria, such as ceria, magnesia, calcia, hafnia, or other known stabilizing additives.

Figure 2:
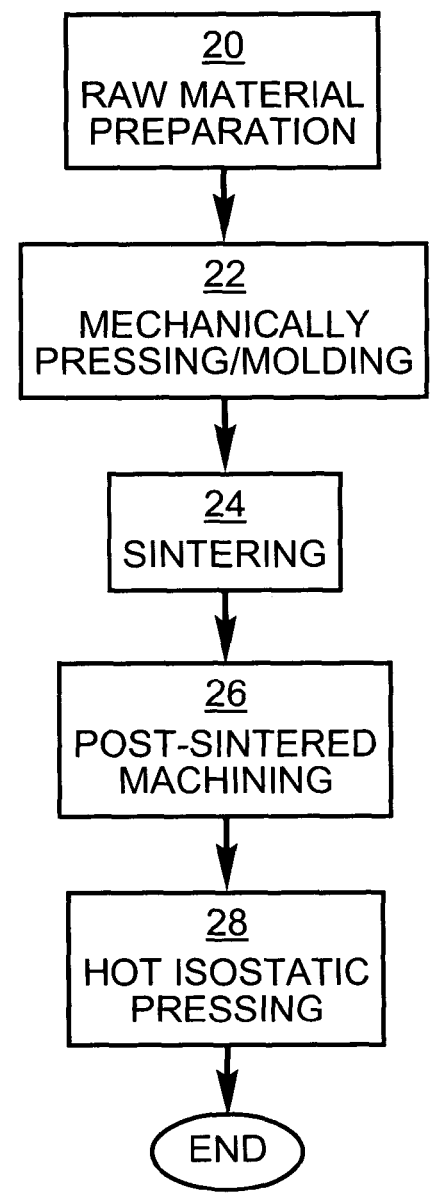
FIG. 2 presents the ceramic processing method steps to form the improved material.

The Y-TZP ceramic tube 4 is formed by conventional ceramic forming processes as shown in FIG. 2, preferably including pressing 22 and sintering 24. The method of forming the tube includes raw material preparation 20, which includes particle size control and binder selection and introduction, as well as selecting the yttria powder and stabilizer. Post-sintering the dense ceramic is optionally machined 26 to final dimensions and required surface finish. The ceramic tube 4 is next further processed by hot isostatic pressing (HIPping) 28 or other known densification methods.

Figure 3:
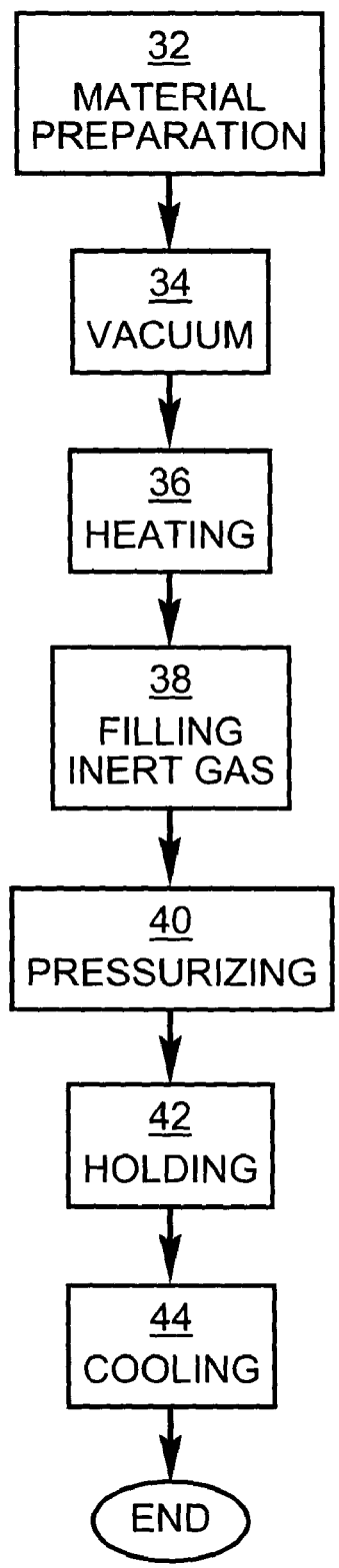
FIG. 3 presents the hot isostatic pressing method steps.

The dense formed ceramic tube 4 is processed according to FIG. 3, where the part is processed 32 by cleaning and is placed in a vacuum 34. The ceramic tube 4 is then heated 36 to 1200° C. to 1450° C. and inert gas is placed in the chamber. It is preferred that argon be used, although other inert gasses may also be selected, as well as selecting a mixture of an inert gas and oxygen, preferably 80 volume percent argon and 20 volume percent oxygen. The chamber is pressurized 40 to preferably approximately 100 MPa, although higher pressures may be utilized to achieve optimum materials properties, and the part is held at temperature and pressure for approximately 30 minutes, although shorter or longer hold times may alternatively be used depending on the selected temperature and pressure. The process chamber and ceramic tube 4 are cooled 44 and the tube 4 is removed and is ready for assembly into the microstimulator 2.

The finished ceramic tube 4 has been post-processed examined to assure that the low-temperature phase transformation has been controlled. Sealed empty brazed cases were used in the in vitro accelerated aging test. Aging treatments were carried out in temperature-controlled ovens and in autoclaves. Low-temperature ceramic degradation was quantified by determining the monoclinic volume fraction ($X_m$) on the ceramic surface of the finished ceramic tube 4. $X_m$ was measured using an X-ray diffraction (XRD) technique and its volume content was calculated from the modified Garvie-Nicholson equation, i.e., $X_m = I_m/(I_m + I_t)$, where $I_m$ is the area under the peak curve for monoclinic phase zirconia as measured by XRD techniques and $I_t$ is the area under the peak curve for tetragonal phase zirconia.

EXAMPLE 1

As-sintered ceramic tubes having a length of 11.7 mm, an outside diameter 2.3 mm and a wall thickness of 0.5 mm and hot isostatically pressed (HIPped) ceramic tubes having the same size and made in the same batch were soaked in 127° C. steam. X-Ray Diffraction was used to measure the surface monoclinic phase and the monoclinic volume fraction was calculated from the modified Garvie-Nicholson equation.

After soaking in 127° C. steam for 171 hours, the monoclinic content on the surface of as-sintered ceramic tubes reached 35% from its original monoclinic content of 2.0%. After the same period of time soaked in the same environment, the monoclinic content on the HIPped ceramic tubes reaches 22% from 0.6% prior to soaking.

XRD analysis showed that although both HIPped and as-sintered ceramics are subject to moisture-induced tetragonal to monoclinic phase transformation, the transformation rate in HIPped TZP was significantly slower than that demonstrated by non-HIPped TZP.

The HIPping process virtually eliminated porosity of the sintered material, improving flexural strength and fracture toughness. The HIPping operation enhanced the aging resistance. The HIPped Y-TZP is much denser than the as-sintered TZP material, with measured bulk density of about 6.05 g/cm$^3$, compared to the specific gravity of 6.10.

As an additional post-HIPped process, the ceramic tube may be loaded in a flexural bending mode so as to pre-load the tube at a known stress. The stress for this proof test type of qualification is preferably 800 MPa, although higher or lower stresses may be used to either change the acceptance rate or to assure a different minimum failure strength. Because of the small size of the tube, three-point bending is utilized to preload the tube, although four-point bending would preferably be used with a longer sample. Tubes that fail to survive the pre-load are thus culled from the sample population thereby giving a minimum strength for the survivors.

Obviously, many modifications and variations of the present invention are possible in light of the above teachings. It is therefore to be understood that, within the scope of the appended claims, the invention may be practiced otherwise than as specifically described.

What is claimed is:

1. A method of producing a long-lived, stabilized tetragonal zirconia polycrystal ceramic, comprising the following steps:
    hot isostatic pressing said ceramic at a controlled temperature, at a controlled pressure, and in a controlled atmosphere to achieve an average grain size of less than about 0.5 micron, to substantially eliminate open porosity and to increase bulk density to about 100% of theoretical, thereby substantially eliminating low-temperature degradation of said polycrystal ceramic; and
    providing said ceramic as an implantable hollow tube.

2. The method according to claim 1 further comprising the step of stabilizing said stabilized tetragonal zirconia polycrystal ceramic with yttria.

3. The method according to claim 2, wherein said step of stabilizing said ceramic with 3 mole percent of yttria.

4. The method according to claim 1 further comprising the step of providing said hollow tube having a length less than 100 mm, an outside diameter less than 10 mm and a wall thickness less than 2 mm.

5. The method according to claim 1 comprising the step of hot isostatic pressing at said controlled temperature of 1200° C. to 1450° C.

6. The method according to claim 1 comprising the step of hot isostatic pressing at said controlled pressure of at least 100 MPa.

7. The method according to claim 1 comprising the step of hot isostatic pressing at said controlled atmosphere in argon.

8. The method according to claim 1 comprising the step of hot isostatic pressing at said controlled atmosphere in a mixture of 80 volume percent argon and 20 volume percent oxygen.

9. A method of producing a long-lived, implantable case, said implantable case comprised of a stabilized tetragonal zirconia polycrystal ceramic, wherein the improvement comprises the step of hot isostatic pressing said implantable case at a controlled temperature, at a controlled pressure, and in a controlled atmosphere to achieve an average grain size of less than about 0.5 micron, to substantially eliminate open porosity and to increase bulk density to about 100% of theoretical, thereby substantially eliminating low-temperature degradation of said implantable case.

10. The method according to claim 9 further comprising the step of stabilizing said stabilized tetragonal zirconia polycrystal ceramic with yttria.

11. The method according to claim 10, wherein said step of stabilizing said ceramic with 3 mole percent of yttria.

12. The method according to claim 9 further comprising the step of providing said implantable case as a hollow tube.

13. The method according to claim 12 further comprising the step of providing said hollow tube having a length less than 100 mm, an outside diameter less than 10 mm and a wall thickness less than 2 mm.

14. The method according to claim 9 comprising the step of hot isostatic pressing at said controlled temperature of 1200° C. to 1450° C.

15. The method according to claim 9 comprising the step of hot isostatic pressing at said controlled pressure of at least 100 MPa.

16. The method according to claim 9 comprising the step of hot isostatic pressing at said controlled atmosphere in argon.

17. The method according to claim 9 comprising the step of hot isostatic pressing at said controlled atmosphere in a mixture of 80 volume percent argon and 20 volume percent oxygen.

18. A method of producing a long-lived, living tissue implantable microstimulator substantially encapsulated within a hermetically-sealed housing, said housing comprised of an yttria-stabilized tetragonal zirconia polycrystal ceramic hollow tube, said microstimulator being of a size approximately 10 mm in diameter and 100 mm in length and of longitudinal shape capable of implantation in the immediate vicinity of selected areas of the body by expulsion through a hypodermic needle, a first inert, metallic electrode hermetically sealed to said housing at or near one end thereof and a second inert, metallic electrode hermetically sealed to said housing at or near another end thereof, and a substantial portion of said electrodes being exposed outside said microstimulator so as to provide stimulation pulses, wherein the improvement comprises the step of hot isostatic pressing said yttria-stabilized tetragonal zirconia polycrystal ceramic hollow tube at a controlled temperature, at a controlled pressure, and in a controlled atmosphere to achieve an average grain size of less than about 0.5 micron, to substantially eliminate open porosity and to increase bulk density to about 100% of theoretical, thereby eliminating low-temperature degradation of said ceramic hollow tube.

19. The method according to claim 18 comprising the step of hot isostatic pressing at said controlled pressure of 100 MPa.

20. The method according to claim 18 comprising the step of hot isostatic pressing at said controlled temperature of greater than 1000° C.

21. The method according to claim 18 comprising the step of hot isostatic pressing in said controlled atmosphere of argon.

22. A method of producing a long-lived, implantable case, said implantable case comprised of a stabilized tetragonal zirconia polycrystal ceramic, comprising the steps of:
    forming said implantable case sized to have a length less than 100 mm, an outside diameter less than 10 mm and a wall thickness less than 2 mm;
    sintering said case to an open porosity of less than 2%;
    hot isostatically pressing said implantable case at a controlled temperature, at a controlled pressure, and in a controlled atmosphere to achieve an average grain size of less than about 0.5 micron, to substantially eliminate open porosity and to increase bulk density to about 100% of theoretical, thereby substantially eliminating low-temperature degradation of said implantable case;
    polishing said ceramic tube to a surface finish of less than 32 microinch roughness; and
    brazing hermetically sealed metal ends on said implantable case.

23. The method of claim 22, further comprising the step of loading the implantable case in three-point bending to a stress of at least 800 MPa to assure that said case will not fail at a lesser stress.

24. The method of claim 22, wherein said step of hot isostatically pressing further comprises hot isostatically pressing at a controlled temperature of 1200° C. to 1450° C.

25. The method of claim 22, wherein said step of hot isostatically pressing further comprises hot isostatically pressing at a controlled pressure greater than 100 MPa.

26. The method of claim 22, wherein said step of hot isostatically pressing further comprises hot isostatically pressing in a controlled atmosphere of argon.

27. The method of claim 22, further comprising the step of hot isostatically pressing at said controlled temperature, said controlled pressure, and said controlled atmosphere for at least 30 minutes.

* * * * *